United States Patent [19]

Eggensperger et al.

[11] 3,988,452
[45] Oct. 26, 1976

[54] PRESERVING AND DISINFECTING COMPOSITION
[75] Inventors: Heinz Eggensperger, Hamburg; Karl-Heinz Diehl, Norderstedt, both of Germany
[73] Assignee: Sterling Drug Inc., New York, N.Y.
[22] Filed: Mar. 5, 1975
[21] Appl. No.: 555,441

[30] Foreign Application Priority Data
Mar. 6, 1974  Germany.............................. 2410606

[52] U.S. Cl. .............................. 424/246; 424/339; 424/341; 424/342
[51] Int. Cl.² .......................................... A61K 31/54
[58] Field of Search .................................... 424/246

[56] References Cited
UNITED STATES PATENTS
3,629,250  12/1971  Mutsch et al. ...................... 424/246
3,655,657  4/1972  Adams ................................ 424/246

Primary Examiner—Sam Rosen
Attorney, Agent, or Firm—Frederik W. Stonner; B. Woodrow Wyatt

[57] ABSTRACT

This invention provides a composition comprising a synergistic combination of (a) a product obtained by reacting formaldehyde with an alcohol selected from benzyl alcohol, a glycol or a glycol mono-alkyl ether, or mixtures of said alcohols, and (b) a 3,5-bis(alkoxyalkyl)-tetrahydro-2H-1,3,5-thiadiazine-2-thione useful in preserving and/or disinfecting industrial fluids, cosmetics and pharmaceutical preparations.

7 Claims, No Drawings

PRESERVING AND DISINFECTING COMPOSITION

BACKGROUND OF THE INVENTION

1. Field of the Invention

The invention relates to antimicrobial compositions which comprise a synergistic combination of a product derived by reacting formaldehyde with an alcohol; and a tetrahydro-2H-1,3,5-thiadiazine-2-thione, useful in controlling the propagation and growth of bacteria and fungi in a variety of industrial fluids and cosmetic and pharmaceutical preparations.

2. Description of the Prior Art

The use of products derived from the reaction of aldehydes with alcohols, for example, such as the formal of benzyl alcohol or the acetals of glycols and glycol ethers, for the preservation and disinfection of industrial fluids is known. Since these compounds are deficient in their microbiocidal activity with respect to fungi and yeasts, they are usually combined with another active ingredient, pentachlorophenol. However, due to the toxicity to warm blooded animals of pentachlorophenol, and the fact that chlorinated phenols are not readily biodegradable, there is a great need for compositions, comprising mixtures of active ingredients, which have a broad spectrum of antimicrobial effectiveness, including effectiveness against various fungi, without having disadvantages such as those associated with the chlorinated phenols.

The fungicidal effectiveness of 3,5-disubstituted-tetrahydro-2H-thiadiazine-2-thiones against certain fungi is known. It is also known that tetrahydro-2-H-thiadiazine-2-thiones, when employed in cooling lubricants together with reducing agents, can undergo reduction with the formation of colloidal sulfur, an undesirable result.

SUMMARY OF THE INVENTION

In a composition aspect of the invention there are provided compositions for controlling the propagation and growth of bacteria and fungi which comprises a combination of:
a. a product obtained by reacting formaldehyde with a monohydric alcohol or dihydric alcohol selected from the group consisting of benzyl alcohol, a glycol having from two to eight carbon atoms, and a mono-alkyl ether of said glycol, wherein alkyl has from one to six carbon atoms, or a mixture of said alcohols, in the ratio of one to two moles of formaldehyde for each mole of hydroxyl group present in said alcohol; and
b. a 3,5-bis(R-O-A)-tetrahydro-2H-thiadiazine-2-thione, wherein R is alkyl having from one to three carbon atoms, and A is alkylene having from two to six carbon atoms; the ratio of (a) to (b) being from about 1 : 99 to about 99 : 1.

The compositions of the invention are useful as antimicrobial agents for preserving and/or disinfecting industrial fluids, and cosmetic and pharmaceutical preparations.

DETAILED DESCRIPTION INCLUSIVE OF THE PREFERRED EMBODIMENTS

The 3,5-bis(R-O-A)-tetrahydro-2H-1,3,5-thiadiazine-2-thiones [component (b)] employed in the compositions of the invention are novel compounds which are described and claimed in our copending application Ser. No. 555,440, filed Mar. 5, 1975, now U.S. Pat. No. 3,946,006. They are prepared by a well known procedure in which initially 2 moles of alkoxyalkylamine of the formula $R-O-A-NH_2$ are reacted in a suitable solvent such as an alkanol, e.g., ethanol, with 1 mole of carbon disulfide at about 20° to 30° C. followed by reaction with two moles of formaldehyde at about 50° to 60° C., the total time of reaction requiring about 1½ to 2 hours. Isolation of the product is carried out using standard procedures.

The reaction products of formaldehyde and alcohol [component (a)] employed in the compositions of the invention are the formals of said alcohols, or mixed formals where mixtures of two or more alcohols are used in the reaction, or hemi-formals. In the case where aqueous fluids, etc., are to be preserved, good solubility of the compositions of the invention in water is required, and for this purpose component (a) preferably is the hemi-formal of an appropriate alcohol, with the hemi-formal of triethylene glycol being particularly preferred. Generally, component (a) is prepared by heating formaldehyde (as paraformaldehyde) with the alcohol, in appropriate molar ratio, in the presence of potassium carbonate at about 70° C. for about 1 hour. The resulting product is filtered and used as such in preparing the compositions of the invention. As will be appreciated, the molar ratio of formaldehyde to alcohol employed in the reaction depends on the number of hydroxyl groups per mole of each alcohol used in any given reaction, one to two moles of formaldehyde being employed for each mole of "hydroxyl." When formation of a hemi-formal is desired, the molar ratio of formaldehyde to each hydroxyl in the alcohol used is about 1 : 1.

As used in this specification, the term alkylene, as represented by A, means such a group containing from two to six carbon atoms having its two free valence bonds on different carbon atoms, for example, $-CH_2CH_2-$, $-CH(CH_3)CH_2-$, $-CH_2CH(CH_3)-$, $-C(CH_3)_2CH_2-$, $-CH_2CH_2CH_2-$, $-CH_2CH(CH_2CH_3)-$, $CH_2CH(CH_2CH_2CH_3)-$, and $-CH_2CH_2CH_2CH_2 CH_2CH_2-$; and the term alkyl, as represented by R, means methyl, ethyl, propyl and isopropyl.

As used in this specification the term glycol means a dihydric alcohol having from two to eight carbon atoms selected from alkylene glycols, dialkylene glycols, and trialkylene glycols as illustrated by ethylene glycol, 1,2-propanediol, 1,2-butanediol, 1,3-butanediol, 1,4-butanediol, 2-methyl-2,3-butanediol, 2,3-dimethyl-2,3-butanediol, 2-methyl-1,2-pentanediol, 1,6-hexanediol, 1,8-octanediol in the case of alkylene glycols; diethylene glycol, dipropylene glycol, 2-(2-hydroxypropoxy)-1-propanol and dibutylene glycol in the case of dialkylene glycols; and triethylene glycol in the case of trialkylene glycols; and the term "mono-alkyl ether of said glycol" means such mono-alkyl ethers wherein alkyl has from one to six carbon atoms, which can be straight or branched, as illustrated by methyl, ethyl, propyl, isopropyl, butyl, tertiary-butyl, pentyl and hexyl.

A preferred glycol is triethylene glycol; and a preferred glycol mono-alkyl ether is the mono-alkyl ether wherein alkyl has from one to four carbon atoms, ethylene diglycol monobutyl ether being especially preferred.

A preferred ratio of component (a) to component (b) in the composition of the invention is from about 1 : 1 to about 9 : 1.

The compositions of the invention possess useful antimicrobial activity, thus indicating the use of these compositions as antimicrobial agents. As used in this specification, antimicrobial means antibacterial and antifungal.

The compositions of the invention have a broad spectrum of antimicrobial activity, are readily biodegradable, and are less toxic to warm blooded animals than the chlorinated phenols. When used in preserving cooling lubricants wherein reducing agents are present, the tetrahydrothiadiazine-2-thione component of the compositions of the invention does not undergo reduction to give colloidal sulfur.

It has surprisingly been discovered that the compositions of the invention exhibit a synergistic effect against bacteria and fungi when compared with the antimicrobial effect of the individual components of said compositions.

The compositions of this invention can be utilized for disinfecting and/or preserving industrial fluids, such as aqueous coating agents, cooling lubricants, e.g., cutting oil emulsions, adhesive solutions and dispersions, and anhydrous pigmented and non-pigmented lacquer systems. They can also be utilized for disinfecting inanimate surfaces and for preserving certain pharmaceutical and cosmetic preparations. In utilizing the compositions of the invention, they can be formulated by preparing a dilute solution in an aqueous medium, containing, if desired, a surfactant, conventional carriers or adjuvants. In utilizing the compositions of the invention for preserving and/or disinfecting industrial fluids, and pharmaceutical and cosmetic preparations, they are added to such fluids and preparations in effective preserving and disinfecting amounts without formulation or, if desired, formulated as described hereinbefore. In utilizing the hereinbefore described formulations for disinfecting surfaces, they can be applied by conventional means such as spraying, swabbing and immersion. For this purpose, the compositions of the invention can be formulated as aerosol sprays or foams.

Generally, when utilized for preserving industrial fluids, and pharmaceutical and cosmetic preparations, and when being formulated for treating inanimate surfaces, the compositions of the invention are employed in from about 0.05 to 0.15 percent concentration.

The bacteriological effectiveness of the compositions of the invention was determined with reference to minimal inhibiting concentrations, that is, the minimal concentration that will effect complete inhibition of germ growth (MIC). The test procedure is as follows:

A 1% suspension, obtained by homogenizing 500 mg. of the test agent in 50 ml. of 0.5% natrosol solution (natrosol 250 HRPS = hydroxymethylcellulose), is serially diluted with 0.5% natrosol solution to provide suspensions, in sterile test tubes, having concentrations of 0.1%, 0.5%, 0.01% and 0.005%. To ensure accuracy in dilution, the suspensions are mixed with the aid of a mechanical mixer. The dilutions (6 ml.) are added to sterile cups and immediately 10 filter discs ($\phi$ about 10 mm) are placed on the surface of the liquid in each cup. The filter discs, which slowly sink to the bottom on becoming saturated, are left in the solutions for one hour. 16-Hour old cultures of *Escherichia coli*, *Staphylococcus aureus*, *Pyoceanus fluorescens* and *Proteus vulgaris* are diluted at the ratio of 1 : 10 in glucose broth. 1-Week cultures of *Penicillium glaucum*, *Aspergillus niger*, *Chaetomium globosum*, *Trichoderma viride*, *Humicola sp.*, *Scopulariopsis brevicaulis*, *Pullularia pullulans*, *Sclerophoma pityophila*, *Saccharomyces cerevisiae* and *Candida albicans* are harvested by rinsing and diluted 1 : 10 in nutrient broth.

Standard II nutrient agar plates, with an addition of lactose and bromomothymol blue (BROLAC agar) for bacteria, and Sabouraud agar plates for yeasts and fungi, are dried and labeled (10 Sabouraud agar plates and 4 nutrient agar plates were used per preparation). Of the diluted germ suspensions, 0.05 ml (1 drop) is inoculated onto each plate. Prior to further treatment, the plates are allowed to stand for one-half hour to absorb the germ suspension. Filter discs, corresponding to each of the five dilutions, are placed on the surface of each inoculated plate for each culture (step 1). The plates are examined for zones of inhibition after 24 hours incubation in the case of bacteria, and after 3 days incubation in the case of yeasts and fungi. Antimicrobial activity is indicated by occurrence of a zone of inhibition. In the case of bacteria, the purity of the culture can be determined at the same time by lactose fermentation as indicated by color change in the nutrient medium. A visible inhibition ring is designated as negative growth an no inhibition ring as 3+ growth. If a test agent exhibits good growth inhibition associated with good capacity for diffusion, it can occur that the test agent, at the highest concentration tested, inhibits the growth on the entire surface of the nutrient medium, and therefore the MIC cannot be ascertained from that particular test. A new dilution series then is prepared, with only one, or at most two, filter discs being placed on the surface of each plate for each culture. Activity is then determined as described above.

The MIC values, expressed as percent concentration, for individual components (a) and (b) and compositions of the inventions are presented in Table I.

In Tables I, II and III which follow, the individual components (a) and (b) and compositions of the invention are identified by appropriate example number corresponding to the specific examples described hereinafter.

Table I

| Micro-organism | MIC Values (% conc.) Test Agent | | | | | |
|---|---|---|---|---|---|---|
| | Ex.1 | Ex.2 | Ex.3 | Ex.4 | Ex.5 | Ex.6 |
| S. aureus | 0.07 | 0.05 | 0.02 | 0.02 | 0.01 | 0.01 |
| E. coli | 0.1 | 0.1 | 0.02 | 0.02 | 0.02 | 0.05 |
| P. fluorescens | 0.1 | 0.1 | 0.05 | 0.02 | 0.02 | 0.05 |
| P. vulgaris | 0.1 | 0.1 | 0.02 | 0.02 | 0.02 | 0.07 |
| P. gluacum | 0.05 | <0.005 | 1 | 1 | 0.002 | 0.005 |
| A. niger | 0.1 | 0.03 | 0.2 | 0.1 | 0.005 | 0.005 |
| S. pityophila | 0.005 | <0.005 | 0.2 | 0.1 | 0.001 | 0.005 |
| P. pullulans | 0.05 | <0.005 | 0.1 | 0.05 | 0.002 | 0.005 |
| S. cererisiae | 0.01 | 0.05 | 1 | 0.5 | 0.002 | 0.002 |

Table I-continued

| | MIC Values (% conc.) Test Agent | | | | | |
|---|---|---|---|---|---|---|
| Microorganism | Ex.1 | Ex.2 | Ex.3 | Ex.4 | Ex.5 | Ex.6 |
| C. albicans | 0.05 | 0.05 | 0.5 | 0.2 | 0.002 | 0.07 |

The antimicrobial effectiveness of the compositions of the invention was also determined in a preservation test in which the effectiveness of the compositions in preserving water miscible cooling lubricants was examined under conditions paralleling as nearby as possible actual use conditions. In this test, cooling lubricants in appropriate dilutions are mixed with varying concentrations of the test agent. The test samples are challenged with periodic inoculations of microorganisms. Smears concurrently are prepared of the individual test samples and the effectiveness of the test agent is evaluated on the basis of the microbial growth of the smears. A test agent is judged to be the more effective, the greater the elapsed time until the first appearance of microbial growth. A description of the test procedure follows.

a. Cultivation of the innoculation solution

In the cultivation of the inoculation solution, consideration is given to whether a cooling lubricant has a mineral oil base, is a semi-synthetic cooling lubricant, or is a mineral oil-free synthetic cooling lubricant. The medium for the microorganisms is chosen according to the composition of the cooling lubricant to be analyzed and 2–4% dilutions thereof are prepared. The solutions of cooling lubricant are inoculated once a week with germs previously cultivated on plates. To parallel actual use conditions, the inoculation solution must contain the following germs:

| 1) Bacteria: | 2) Fungi |
|---|---|
| Escherichia coli | Aspergillus sp. |
| Pseudomonas aeruginosa | Penicillium sp. |
| Proteus vulgaris | Fusaria |
| Bacilli | different yeasts. |
| different gram-negative rods | |
| dye generators | |

The inoculation solution thus prepared is ventilated in a water bath at 35° C in inverted washing flasks in day and night cycles. Once each week, 20% of the total inoculation solution is discarded and replaced by freshly prepared dilutions of cooling lubricant. This ensures that the germ content of the inoculation solution remains above $10^6$ germs per ml and that there is no selection of individual germ types.

b. Test procedure

Dilutions (50 ml) of cooling lubricant are prepared in standard concentrations. To these dilutions are added the test agents in appropriate use concentrations. A non-preserved dilution of cooling lubricant serves as growth control. The test samples are mixed twice a week with 1% inoculation solution. Cast-iron splinters ($1_g$) are added to each sample.

To parallel actual use conditions, the dilutions of cooling lubricant in 200 ml Erlenmeyer flasks are agitated during the day on a shaking machine and to ensure gas exchange, the flasks are not closed. During the night the samples are not agitated. The evaporation and discharge losses of the dilutions of cooling lubricant are replaced once a week with tap water (hardness 20°).

Each time immediately prior to a new inoculation, smears are prepared twice a week on glucose and Sabouraud agar plates. These smears are incubated at 35° C. for detecting bacteria and at 22° C. for detecting fungi and plates are evaluated for growth after 35 or 72 hours incubation respectively. The degree of microbial growth is evaluated semi-quantitatively on a scale: −, +, ++, +++. The end of the preserving action is indicated by repeatedly demonstrated, massive germ growth. The results obtained in this test are presented in Table II wherein the concentration of test agent is given as percent, and "Germ Inhibition (Days)" denotes the elapsed time in days until the end of the preserving action, as determined according to the procedure described above.

Table II

| | Test Agent | Conc. (%) | Germ Inhibition (Days) |
|---|---|---|---|
| A) Cooling lubricant with mineral oil base | Ex.1 | 0.1 | 12 |
| | Ex.2 | 0.1 | 10 |
| | Ex.3 | 0.15 | 8 |
| | Ex.4 | 0.15 | 6 |
| | Ex.5 | 0.15 | 30 |
| | Ex.6 | 0.15 | 25 |
| B) Cooling lubricant without mineral oil base | Ex.1 | 0.1 | 15 |
| | Ex.2 | 0.1 | 13 |
| | Ex.3 | 0.15 | 10 |
| | Ex.4 | 0.15 | 10 |
| | Ex.5 | 0.15 | 35 |
| | Ex.6 | 0.15 | 37 |

The effectiveness of the compositions of the invention was also established in a preserving test in which the effectiveness of chemical preservative agents with respect to in-container preservation of dye dispersions was evaluated. For this purpose, test samples are prepared by addition of the test agent in varying concentrations to unpreserved paint formulations. The test samples are challenged by periodic inoculations with microorganisms. The inoculated test samples are evaluated for surviving microorganisms by means of the streak plate subculture technique. The length of time during which microbial growth is not detectable is used as a relative measure of preservation activity.

In carrying out this test, 50 g samples of the dispersion dye are added to screw-top jars. The test agent is added to the test samples in its proper use concentration. The concentrations are so chosen that they bracket the average use concentration. An unpreserved dispersion dye serves as the growth control.

Two days following the addition of the test agent, the test samples are inoculated with 0.2 ml of a suspension of the test microorganisms. The titer of the inoculum should be at least $10^6$ microorganisms per ml. The samples are reinoculated at weekly intervals. The streak plates are prepared twice weekly and evaluated for growth after 3 days of incubation at 22° C. If negative results are obtained, the streak plates are incubated an additional 2 days and then reevaluated. The subculturing is carried out on glucose agar plates. The degree of microbial growth is evaluated semi- on a scale: —, +, ++, +++. A +++ reading indicates extensive microbial growth and the end of preservation action.

The inoculum for the foregoing described test was prepared as follows.

Microorganisms, such as *Pseudomonas aerug.*, *Proteus sp*, *Escherichia coli* and yeasts, are cultured on the surface of glucose-agar plates. Three day old cultures are rinsed off with physiological saline solution and filtered through glass wool. Molds are cultivated on agar slants and added to the inoculation suspension by means of a platinum-wire loop.

The inoculum suspension contains the following microorganisms (bacteria, yeasts and molds): *Pseudomonas aeruginosa; Proteus vulgaris; Klebsiella aerobacter; Escherichia coli;* various yeasts; *Aspergillus niger; Penicillium glaucum:* Mucor; *Pullularia pullulans.*

A preservative agent is judged to be satisfactory under the conditions specified above, if the test samples remain free of appreciable microbial growth for a period of 6 to 8 weeks. Excellent preservative agents can under these conditions maintain test samples free from microbial growth for 10 or more inoculation cycles.

The results of this test are presented in Table III wherein the concentration of the test agent is given in percent and "Inoculation Cycles" denotes the number of inoculation cycles (corresponding to the number of weeks) during which samples remained free of microbial growth, as determined according to the procedure described above.

Table III

| Test Agent | Conc. (%) | Inoculation Cycles |
| --- | --- | --- |
| Ex.2 | 0.5 | 4 |
| Ex.3 | 0.1 | 2 |
| Ex.4 | 0.1 | 2 |
| Ex.5 | 0.1 | 11 |
| Ex.6 | 0.1 | 10 |

The invention is illustrated by the following examples without, however, being limited thereto.

Preparation of Component (b)

EXAMPLE 1

3,5-Bis(2-methoxyethyl)-tetrahydro-2H-1,3,5-thiadiazine-2-thione 30 g (0.4 mole) 2-methoxyethylamine in 200 ml ethanol was treated dropwise, with stirring and cooling, with 15.2 g (0.2 mole) carbon disulfide. Stirring was continued for 20 minutes and then 12.5 g (0.4 mole) paraformaldehyde was added and stirring was continued an additional one hour at 50°–55° C. The reaction solution was concentrated under reduced pressure to give the title compound as a light yellow, lightly viscous liquid. (Yield: 93% of theory). Anal. Calcd for $C_9H_{18}N_2O_2S_2$: N, 11.2; S, 25.6. Found: N, 10.6; S, 25.2.

EXAMPLE 2

3,5-Bis(3-methoxypropyl)-tetrahydro-2H-1,3,5-thiadiazine-2-thione 35.6 g (0.4 mole) 3-methoxypropylamine in 200 ml ethanol, was treated dropwise, with stirring and cooling, with 15.2 g (0.2 mole) carbon disulfide, the temperature being maintained at about 20°–25° C. After the addition was completed, stirring was continued for about an additional thirty minutes at room temperature. 12.5 g (0.4 mole) paraformaldehyde was then added and stirring was continued for another two hours at 50°–55° C. The reaction solution was concentrated under reduced pressure and the residue obtained was filtered, to give 53.5 g of the title compound as a clear yellow oil. (Yield: 97% of theory). Anal. Calcd for $C_{11}H_{22}N_2O_2S_2$: N, 10.06; S, 23.03. Found: N, 10.31; S, 22.90.

Preparation of Component (a)

EXAMPLE 3

Mixed formal with benzyl alcohol and diethylene glycol monobutyl ether

1 Mole diethylene glycol monobutyl ether and 1 mole benzyl alcohol are heated to 70° C with 2.5 mole paraformaldehyde after adding about 1 g potassium carbonate and stirred for 1 hour at said temperature. After cooling, the mixture is filtered and used without purification in the compositions of the invention.

EXAMPLE 4

Hemi-formal of triethylene glycol

Following the general procedure described in Example 3 but substituting one mole of triethyleneglycol for the diethylene glycol monobutyl ether and benzyl alcohol, and using one mole of paraformaldehyde there is obtained the title product.

Following the general procedure described in Example 3, formals and mixed formals with benzyl alcohols, glycols and glycol mono-alkyl ethers can be obtained.

PREPARATION OF THE COMPOSITIONS OF THE INVENTION

The compositions of the invention are prepared by stirring together components (a) and (b), in the desired weight ratios, until a homogeneous mixture is obtained. In this manner, the following compositions of Examples 5 to 8 were obtained.

EXAMPLE 5

(a) Mixed formal of benzyl alcohol and ethylene diglycol monobutyl ether (Example 3) and (b) 3,5,-bis(3-methoxypropyl)-tetrahydro-2H-1,3,5-thiadiazine-2-thione (Example 2) in a weight ratio of 1 : 1.

EXAMPLE 6

(a) Hemi-formal of triethylene glycol and (b) 3,5-bis(3-methoxypropyl)-tetrahydro-2H-1,3,5-thiadiazine-2-thione in a weight ratio of 1 : 1.

EXAMPLE 7

Components (a) and (b) of Example 1 in a weight ratio of a : b of 9 : 1.

EXAMPLE 8

Components (a) and (b) of Example 1 but in a weight ratio of (a) : (b) of 3 : 1.

We claim:

1. A composition for controlling the growth and propagation of bacteria and fungi which comprises in combination:
   a. a product obtained by reacting formaldehyde with a monohydric alcohol or dihydric alcohol so as to produce a formal or hemi-formal of said alcohols, where said alcohols are selected from the group consisting of benzyl alcohol, a glycol having from two to eight carbon atoms, and a mono-alkyl ether of said glycol, wherein alkyl has from one to six carbon atoms, or a mixture of said alcohols, in the ratio of 1 to 2 moles of formaldehyde for each mole of hydroxyl group present in said alcohol; and b. a 3,5-bis(R-O-A)-tetrahydro-2H-thiadiazine-2-thione, wherein R is alkyl having from one to three carbon atoms, and A is alkylene having from two to six carbon atoms; the ratio of (a) to (b) being from about 1 : 99 to about 99 : 1.

2. A composition according to claim 1 wherein: in (a), the alcohol reacted is triethylene glycol, or a mixture of benzyl alcohol and diethylene glycol monobutyl ether.

3. A composition according to claim 2 wherein the molar ratio of (a) to (b) is from about 1 : 1 to about 9 : 1.

4. A composition according to claim 3 wherein (b) is 3,5-bis(3-methoxypropyl)-tetrahydro-2H-1,3,5-thiadiazine-2-thione.

5. A composition according to claim 4 wherein the molar ratio of (a) to (b) is about 1 : 1.

6. A composition according to claim 5 wherein (a) is the mixed formal of benzyl alcohol and diethylene glycol monobutyl ether.

7. A composition according to claim 5 wherein (a) is the hemi-formal of triethylene glycol.

* * * * *

UNITED STATES PATENT AND TRADEMARK OFFICE
CERTIFICATE OF CORRECTION

PATENT NO. : 3,988,452
DATED : October 26, 1976
INVENTOR(S) : Heinz Eggensperger and Karl-Heinz Diehl It is certified that error appears in the above-identified patent and that said Letters Patent are hereby corrected as shown below:

Column 4, line 18, "bromomothymol" should read -- bromothymol --.

Column 7, line 3, -- quantitatively -- should be inserted after -- semi- --.

Signed and Sealed this

Twenty-sixth Day of April 1977

[SEAL]

Attest:

RUTH C. MASON
Attesting Officer

C. MARSHALL DANN
Commissioner of Patents and Trademarks